United States Patent
Parssinen

(10) Patent No.: US 9,226,846 B2
(45) Date of Patent: Jan. 5, 2016

(54) BANDAGING MATERIAL

(75) Inventor: Antti Parssinen, Espoo (FI)

(73) Assignee: Onbone Oy, Helsinki (FI)

( * ) Notice: Subject to any disclaimer, the term of this patent is extended or adjusted under 35 U.S.C. 154(b) by 183 days.

(21) Appl. No.: 13/821,568

(22) PCT Filed: Sep. 12, 2011

(86) PCT No.: PCT/FI2011/050782
§ 371 (c)(1),
(2), (4) Date: Mar. 8, 2013

(87) PCT Pub. No.: WO2012/032226
PCT Pub. Date: Mar. 15, 2012

(65) Prior Publication Data
US 2013/0172795 A1   Jul. 4, 2013

(30) Foreign Application Priority Data
Sep. 11, 2010  (FI) .................................. 20105941

(51) Int. Cl.
*A61F 5/00* (2006.01)
*A61F 5/05* (2006.01)
*A61L 15/10* (2006.01)
*A61L 15/12* (2006.01)

(52) U.S. Cl.
CPC . *A61F 5/05* (2013.01); *A61L 15/10* (2013.01); *A61L 15/12* (2013.01)

(58) Field of Classification Search
CPC ..... A61F 13/041; A61F 13/043; A61F 13/04; A61F 13/00; A61F 5/00; A61F 5/004
USPC ........................ 602/5–8; 524/13–14; 427/2.31
See application file for complete search history.

(56) References Cited

U.S. PATENT DOCUMENTS

| | | | |
|---|---|---|---|
| 4,019,505 A | * | 4/1977 | Wartman .......................... 602/7 |
| 4,376,438 A | | 3/1983 | Straube et al. |
| 7,323,253 B2 | * | 1/2008 | Isaksson et al. .............. 428/524 |
| 2008/0154164 A1 | | 6/2008 | Sheehan et al. |
| 2008/0262400 A1 | | 10/2008 | Clark et al. |

FOREIGN PATENT DOCUMENTS

| | | |
|---|---|---|
| WO | WO9403211 A1 | 2/1994 |
| WO | WO0035501 | 6/2000 |
| WO | WO2007035875 | 3/2007 |
| WO | WO 2008041215 A1 * | 4/2008 |
| WO | WO2010103186 A2 | 9/2010 |
| WO | WO2010103187 A2 | 9/2010 |

* cited by examiner

*Primary Examiner* — Kim M Lewis
(74) *Attorney, Agent, or Firm* — Seppo Laine Oy

(57) ABSTRACT

A bandaging material in the form of a linear structure. The material has a first layer formed by a composite containing a thermoplastic polymer selected from the group of polymers and mixtures thereof, and a woody material derived from platy or granular wood particles having a minimum average size in one dimension of 0.1 mm. The material further has a second layer of a textile material having a first and a second surface. The first layer is superposed on the second layer in such a way that the first layer is essentially attached only to the first surface of said second layer. In this way, a bandaging material is obtained which has a suitably small self-adhesion which allows for it being coiled to a roll without force during manufacturing process. The bandaging material can further be uncoiled smoothly by hand followed by subsequent applying of it around limb at application temperature without delamination.

17 Claims, No Drawings

BANDAGING MATERIAL

BACKGROUND OF THE INVENTION

1. Field of Invention

The present invention relates, in general, to the forming of a structure on or around a body part of an animal or human being. More specifically, it relates to the field of orthopedic bandaging materials, methods of making the same and uses thereof. Described herein is also a method of using a novel bandaging material in immobilization of a fractured body part.

2. Description of Related Art

Splinting and casting are the two most common methods of externally immobilizing orthopedic injuries. Splinting is the preferred method in the acute short term care setting since a non-circumferential treatment method allows natural swelling, which occurs during the initial inflammatory phase. Furthermore, a splint can be removed more easily than a circumferential cast, allowing regular inspections of the injury site.

However, splinting is not an appropriate treatment method when fractures are potentially unstable (e.g. fractures requiring reduction, segmental or spiral fractures, dislocation fractures) and can be utilized only for acute immobilization to allow swelling while awaiting definitive care. Casting is therefore the mainstay of treatment for most fractures because it generally provides more effective immobilization of the injury. However, this technique requires more skill and time to apply and has a higher risk of complications if not applied properly (e.g. skin breakdown, necrosis, and compartment syndrome).

Both immobilization methods are applicable for several different types of fractures and therefore skin lesions, soft-tissue injuries, and neurovascular status of the involved extremity are carefully documented before selecting splint or cast application.

The materials utilized for commonly used large volume casting applications include the following:

- plain-weave gauze fabrics coated with calcium sulphate hemi-hydrate;
- knitted fibreglass substrates impregnated with a polyurethane resin; and
- knitted polyester fabrics, impregnated with a clear polyurethane resin Although casts manufactured of synthetic materials (DE 26 51 089, U.S. Pat. No. 4,376,438) are lighter, more durable and water resistant than plaster-of-Paris casts (WO 0035501), they are not superior in all respects. Many of the materials are toxic or at least difficult to dispose of. However, also their properties of use are in to some degree inadequate. For example, certain of the synthetic casting materials are considered more difficult to apply than plaster-of-Paris, and the conformability of the synthetic casting materials is reportedly inferior to that of plaster-of-Paris.

A cast which is poorly moulded will loosen more rapidly as soft tissue swelling resolves, and therefore use of synthetic casting materials is not recommended when there is an extensive soft tissue swelling. Also the problem of internal ridging predisposing to skin rubbing occurs more frequently in synthetic casts. In the case of lower limb walking casts, the lower weight of synthetic casts may not have significant dividends in terms of a reduction in the energy required to walk, as other factors, such as the angle of ankle fixation, have been shown to be more important than cast weight.

In addition to the above mentioned synthetic polyurethane products, various composites consisting of polycaprolactone homopolymers (PCLs) and fibrous materials are potentially interesting materials for orthopedic applications (WO 94/03211, WO 2007/035875 and US 2008/0262400). The PCLs have good strength properties and are biologically degradable. However, the PCL/fibrous material combinations do not meet all requirements of casting roll tape material. On the contrary, PCL-natural fiber composites have several disadvantages in a roll form like easy de-laminating feature after hardening, low dimensional stability during heating to application temperature, at application temperature (e.g. Cobra-cast) polymer particles will attach to skin requiring washing, and difficult coiling procedure at application temperature. Also excess of flexibility is found disadvantageous for circumferential casting applications; may cause easily pressure sores.

It is an object of the present invention to eliminate at least a part of the problems related to conventional splinting systems (in particular for circumferential application) and the above-mentioned problems of current products related either to their toxicity, complexity of structures and use or insufficient rigidity for splinting the limbs and body extremities.

SUMMARY OF THE INVENTION

An aspect of the present invention is to achieve a novel bandage material comprising of a wood-plastic composite and a textile which can be heat-molded to the contours of an animal or human body part.

A further aspect of the present invention is to achieve a method of producing the bandage materials as well as a method of using the composite material of the present invention as a splint or circumferential cast to immobilize a body part of an animal or human.

The invention is based on the concept of providing the cast material in the form of a bandage with at least two layers which can be shaped into the desired form of a cast or splint in situ.

The present bandage for an orthopedic cast or splint is, in particular, provided in the form of a linear structure such as a sheet, a ribbon or a tape or a band, comprising of two layers. A first layer composed of a composite material with a first component formed by a polymer and a second component formed by a reinforcing material. The polymer is a thermoplastic polymer preferably selected from the group of biodegradable polymers and mixtures thereof, and the second component comprises a woody material derived from platy or granular wood particles. The composite material is formable at least at a temperature of about 60 to 70° C., although the temperature can be as high as 120° C. without degradation of the composite taking place.

In addition to the composite material, the bandage comprises a second textile layer. The composite material is adhered to one surface of the textile layer such that said first layer is essentially attached only to the one surface of the second layer.

To achieve suitable properties of intralayer vs. interlayer adhesion, the bandaging material can be embossed to reduce self-tack.

Preferably the bandage is provided in the form of a roll having at least 2 coils of the bandage, said coiled bandage exhibiting strong intralayer adhesion and a modest interlayer adhesion, which allows for the roll to be uncoiled at a temperature above the melting or softening point of the thermoplastic but below 80° C. without breaking up of the intralayer structure.

The present bandage can be produced by a method comprising the steps of providing the material of the first layer by mixing together a first component selected from the group of biodegradable polymers and mixtures thereof with a reinforcing material selected from woody materials in the form of platy and granular wood particles to produce a composite material, said mixing being carried out as melt mixing in an apparatus for melt processing of polymers. The melt composite material is provided in the form of a layer having a linear structure. A second layer of a textile material having a first and a second surface is also provided; and the first and the second layers are fitted in superposed relationship; and pressed to each other at a temperature in excess of 80° C. so as to provide a bandaging material in which the first layer is essentially attached only to the first surface of said second layer.

The material can be used in a method of shaping a composite material to snugly fit against a part of the body of a mammal, comprising the steps of providing the composite material in the form of a bandage of the present kind, heating the bandage to a temperature in the range of 58 to 120° C., in practice typically 58 to 80° C. or less than 80° C. and preferably about 65 to 70° C., to convert the composite material of the bandage into a manually formable state, applying the material against the target part of the body to as to make the material take up the form of the target part, and cooling the material to a temperature of less than 45° C. to make the material rigid.

The method can comprise an embodiment for forming a removable exo-skeletal device on a portion of a body of a human or animal, the method comprising the steps of;
  providing a bandage material;
  heating the bandage material in a heating device to a temperature high enough to soften the composite material yet not so high as to be harmful to skin of the human or animal;
  arranging the softened bandage material on the desired portion of the body of the human or animal so that it conforms to the desired three-dimensional contoured exo-skeletal shape; and
  cooling the contoured exo-skeletal composite material to a temperature approximating the ambient temperature such that the contoured exo-skeletal bandage material resumes the same rigidity as the shaped linear composite material prior to heating.

The bandage material of the present invention provides distinct advantages over all prior art materials used for splinting or casting an injured body part.

The present material is the first bandaging material for immobilization of human or animal body parts which is based on a thermoplastic material. By adjusting the amount of wood particles the product will have a property of suitably strong or weak self-adhesion, which can be used for example for coiling and uncoiling of the material, when it is in the form of a roll, during normal use and at application temperature. The material can be used as a rolled material or used as such without coiling the material in to a roll. Coiling and uncoiling of the material is possible because merely one surface of the roll material is "self-adhesive". In other words, the bandage exhibits strong intralayer adhesion (adhesion between the two component layers of the bandage) and a weak to modest interlayer (adhesion between two overlapping or adjacent layers of the bandage). The self-tack of the bandaging material can be even further reduced by providing it with embossing depressions.

By using a slightly elastic textile for the textile layer it is possible to improve anatomic forming after rigidification of the product. Tearing of the new material can also be prevented.

A loose and thin textile (in particular a textile with an open and/or porous structure), with preferably some elastic elongation in at least one direction, will meet the provision.

The wood particles will prevent heat conduction for which reason products can be used at temperatures up to +70° C. without the risk of burning the skin of the patient.

Thus, the present bandage material is easy to work with, has a light weight while maintaining the necessary structural properties of a splint/cast. It is ecologically friendly and is reusable without substantially degrading throughout uses.

A further advantage of the present invention is that the bandage is mouldable at temperatures very comfortable to patient and not scorching the skin of the patient. Furthermore, the bandage, when solidifying, forms a rigid overall structure and does not need any further reinforcement than the natural anatomic shape to build up a reliable immobilization splint for the treatment period.

The bandage, when applied, is capable of taking up a three-dimensional configuration conforming to the desired body contours without undesirable wrinkling or tearing. The bandage can be coiled circumferentially to dimensions close to the assumed size of the treated limb and cut from greater length of the bandage to diminish the amount of waste material. Additionally, the leftover pieces as well as the abandoned and used bandages are fully or partly biodegradable and naturally combustible in the environment, as their main components, wood and polycaprolactone, are fully or at least partly biodegradable and contain no harmful components to human or to environment. In one embodiment, the textile layer is either fully or partly biodegradable or at least combustible.

The bandages can be easily be rolled and stored in compact stacks. When composite casts are packaged appropriately they can be easily stored for at least one year.

After opening the bandage package, the wood like composite plate can be handled without any protection, e.g. gloves and masks, since the component materials are non-toxic. The composite can then be placed in to a heating device having an adjustable thermostat system or a preprogrammed thermostat tailored to the system. The bandage can be heated to an operating temperature of around 65° C., preferably in dry condition, in less than 2 to 20 minutes depending on the heating method. At this temperature, the composite portion of the bandage becomes soft and pliable and the bandage can be applied to the desired body part or region. Due to thermal characteristics of wood or woody components, the splint does not feel hot on a skin of operating personnel or a patient The bandage remains applicable (or pliable) for around 1-10 minutes after heating. During the application time, the bandage can be easily uncoiled and shaped to accurately match an injured body part. The full strength properties of the cast is achieved approximately in 60 minutes after the initial hardening; however the time may be shortened to few minutes when an external cooling system is used. In case the clinical practitioner needs to re-formulate the shape of the cast, it can be easily removed and re-heated to the operating temperature. In this way, an unlimited working period can achieved, which is a clear advantage over the current chemically curable plastic or chalk (POP) casts. It is also a distinctive property of the novel casting system that even if the circumferential cast is moldable during its cooling period down to lower surface temperatures, the hardened cast does not yield or become malleable until the original operating temperature for the cast is again reached.

The entire treatment system is water-free and during heating, applying and use there are no dust, chemicals or vapors released.

The present invention will now be described in more detail with the aid of a detailed description of the preferred embodiments.

DETAILED DESCRIPTION OF PREFERRED EMBODIMENTS

As discussed above, the present materials comprise bandages which have at least two layers, at least one of a textile material and at least one of a novel polymer-wood particle composite.

In a preferred embodiment there is one textile layer to which a composite layer is adhered such that the composite layer is bonded to only one surface of the textile layer. A 2-layered product has been found to have properties quite sufficient for most practical purposes. However, it is also possible to provide a structure having several alternating layers of textile and composite. Thus, there can be generally 2 to 30 layers in the present bandaging material. In one embodiment the multi-layered product has an even number of layers (2, 4, 6, 8, 10 or more). Naturally, it is also possible to provide products having an uneven number of layers, such as 3 or 5 layers or more. As will be explained below, it is also possible to further provide a separate textile or fibrous layer which comes against the skin to further reduce the risk of skin lesions.

The textile layer is typically freely formable and capable of contouring to any part of a human or animal body. Thus, the linear mass density of the fibers of the textile is selected such that the layer is typically not self-supporting. A loose structure is preferred to a dense. It is particularly preferred that the textile layer exhibits flexibility or elasticity in at least one dimension to allow for good fitting against the part of the human or animal body which is to be immobilized. The textile material will be discussed in more detail below.

The composite layer of the bandage is typically rigid below its solidification point. Thus, composite layer of the bandage retains its shape as it cools down. Even if it is substantially rigid it is also flexible so as to be supportive and comfortable. Rigidity is generally achieved when a sample heated to the above indicated softening temperature is cooled to below 50° C., in particular to less than 45° C., preferably less than 40° C. Typically, the composite is rigid at ambient temperature; a suitable temperature of use is about 20 to 50° C., in particular 22 to 40° C.

The properties of adherence of the composite material are of importance, and as will be explained, the present bandaging material is capable of being coiled and—importantly—uncoiled because of the properties of self-adherence of the first layer (strong intralayer adhesion) and weaker adherence of the second layer (modest to weak interlayer adhesion). The composite material of the present invention can be simply manufactured by mixing the first component, i.e. a suitable polymer material for example in the form of pellets, with the second component i.e. wood particles or granules, by melt mixing. The mixing can be carried out in any conventional apparatus designated for melt mixing or melt processing. One example is a heatable vessel having a mechanical stirrer.

The manufactured virgin composite material may be reused by crushing, slicing or cutting the composite material to small pieces and by starting the mixing procedure again.

The uniformity of the composite can be increased by using an extruder, kneader or any device suitable for mixing thermoplastic polymers.

By using an extruder mixing apparatus equipped for example with two hoppers, each containing one of the components of the material, the desired amount of each component can be fed in to the mixing chamber of the apparatus. Then, by way of the mixing means in the mixing apparatus, there is formed a homogeneous mixture of the first and second components prior to the formation of the formation of the material.

One advantage to the material being formed by such a homogeneous mixture of the components is that the forces necessary to form a substantially homogeneous material are reduced. Therefore, little or no compression force is necessary to facilitate mixing of the components in a material formation step. The importance of this factor is that, by way of the homogeneous mixture, larger particles of each component can be used which would otherwise have been destroyed when subjected to high compression forces.

The material mixed with an extruder can be shaped with a nozzle to the shape of e.g. an elongated sheet, mainly of rectangular shape, such as a sheet, a ribbon or a tape or a band. Typically, the layer of composite material, cut to appropriate size, has a width of, for example, 10-150 mm, a length of, for example, 400-3600 mm and a thickness of about 0.5-1.5 mm, the ratio of length to width, L/W, being at least 3:1, for example at least 4:1, or at least 5:1 or at least 6:1 or at least 8:1 or at least 10:1. Generally, the upper limit of the ratio can be 1000:1 although 100:1 is more conventional.

The proportions between the components of the material can vary in a broad range. Thus, generally, 5 to 99 wt-%, for example 40 to 99 wt-%, of the material is formed by the thermoplastic polymer component and 1 to 95 wt-%, for example 1 to 60 wt-%, by the woody material.

The weight ratio of polymer-to-wood can easily be modified and the weight percent of wood, based on the total weight/volume of the composition, may vary between 1 and 70%, preferably however in the range of 10 to 60 weight percent, or 20 to 60 weight percent, and 15 to 50%, or 25 to 50%, by volume.

As will appear from the examples, particularly interesting properties are obtained with 40 to 80 parts by weight, in particular 50 to 80 parts by weight, preferably 55 or 60 to 75 parts by weight, of a thermoplastic polymer component and 20 to 60 parts by weight, in particular 20 to 50 parts by weight, preferably 25 to 40 or 45 parts by weight, of a woody material, the weight of the woody material being calculated based on the dry weight of said wood material.

The second component of the composite comprises or consists essentially of a woody material having a smallest diameter of greater than 0.1 mm. There can also be other wood particles present in the second component. The woody material can be granular or platy. According to one embodiment, the second component comprises a woody material derived from platy wood particles having a smallest diameter of greater than 0.1 mm.

Thus, generally, the wood component can be characterized generally as being greater in size than powder.

The size and the shape of the wood particles may be regular or irregular. Typically, the particles have an average size (of the smallest dimension) in excess of 0.1 mm, advantageously in excess of 0.4 mm, for example in excess of 0.5 mm, suitably about 0.6 to 10 mm. The length of the particles (longest dimension of the particles) can vary from a value of greater than 0.6 mm to value of about 1.8 to 200 mm, for example 3 to 21 mm.

The woody particles can be granular, platy or a mixture of both. Woody particles considered to be granular have a cubic shape whose ratio of general dimensions are on the order of thickness:width:length=1:1:1. In practice it is difficult to measure each individual particle to determine if it is a perfect cube. Therefore, in practice, particles considered to be granular are those where one dimension is not substantially different than the other two.

Woody particles considered to be platy means that they have generally a plate-shaped character, although particles of other forms are often included in the material. The ratio of the thickness of the plate to the smaller of the width or length of the plate's edges is generally 1:1 to 1:500, in particular about 1:2 to 1:50. Preferably, the woody particles include at least 10% by weight of chip-like particles, in which the ratio of general dimension are on the order of thickness:width:length=1:1-20:1-100, with at least one of the dimension being substantially different than another.

Based on the above, the platy particles of the present invention generally comprise wood particles having at least two dimensions greater than 1 mm and one greater than 0.1 mm, the average volume of the wood particles being generally at least 0.1 mm$^3$ more specifically at least 1 mm$^3$.

"Derived from platy wood particles" designates that the wood particles may have undergone some modification during the processing of the composition. For example, if blending of the first and second components is carried out with a mechanical melt-mixing device or with extruder having small nozzle dimensions, some of the original platy wood particles may be deformed to an extent.

The majority of wood particles greater in size than powder, which particles may be granular or platy, typically make up more than 70% of the woody material.

The wood species can be freely selected from deciduous and coniferous wood species alike: beech, birch, alder, aspen, poplar, oak, cedar, *Eucalyptus*, mixed tropical hardwood, pine, spruce and larch tree for example.

Other suitable raw-materials can be used, and the woody material of the composite can also be any manufactured wood product.

The particles can be derived from wood raw-material typically by cutting or chipping of the raw-material. Wood chips of deciduous or coniferous wood species are preferred.

In WO 94/03211 a composite material is described, based upon polycaprolactone, ground almond shell and wood flour. The known material is impaired by several disadvantages, such as a high density of 1.1 kg/m$^3$ or even more, as a result of the small particle sizes of the filler material [wood, less than 600 microns (600 μm)]. Another disadvantage related to the use of small particle sized fillers, is the poor adhesive properties of composite material. According to our findings composites consisting of 40 weight percentage of wood dust sized between 0-800 microns reveal zero adhesion toward a textile material (compression force of 0.1 bars) and is therefore not suitable for the production of bandages of the present type.

The present invention differs from the art in several aspects. A thermoplastic polymer material is typically tacky at a temperature above its melting point. For this reason it is not possible to open up a structure of a neat polymer which is formed by polymer parts bonded to each other without breaking the structure. In the present technology, the tackiness of the polymer is reduced with platy or granular wood particles. The polymer is loaded with such particles up to a point where the surface of the composite material thus formed is only moderately tacky or semi-tacky. By adhering a textile layer to one surface of the composite material, the tackiness can be even further reduced on that surface so as to provide a laminate with surfaces of different tackiness on opposite sides. Such a material is capable of being coiled to a roll at a temperature which is only moderately higher (e.g. about 10 to 20° C.) than the melting point of the polymer. During coiling, there will be restricted self-adherence of the laminate such that the roll can be readily uncoiled, without breaking the structure, when heated to a temperature in the same range.

The uncoiled material can be applied around a body part, e.g. a limb. Suitable lengths of material, typically extending from 5 to 2000 mm, can be cut from the coiled bandage and used for circular casting.

To avoid mobilization of the cast and to improve immobilization of the fractured limb during setting of the bandages moderate adhesion forces are required. In a preferred embodiment of the present technology, in which the textile layer is at least moderately elastic, the bandage is stretched during application by 1 to 75% in at least one direction to promote lamination of the layers to each other in order to produce a circular cast.

Further, the polycaprolactone polymer (CAPA 656) presented in examples of WO 94/03211 has too low viscosity (melt flow index value of 7 g/10 minutes with 2.16 kg standard die at 160° C.) to be used at practical applying temperature of 65° C. The composite manufactured of PCL having MFI value of seven (PCL-7) tears too easily and does not tolerate strong bending during applying.

By contrast, the present composite materials based on a polymer having a higher viscosity/molecular mass provide excellent properties also in this respect.

In addition to wood chips and other platy particles, the present composition can contain reinforcing fibrous material, for example cellulose fibers, such as flax or seed fibers of cotton, wood skin, leaf or bark fibers of jute, hemp, soybean, banana or coconut, stalk fibers (straws) of hey, rice, barley and other crops and plants including plants having hollow stem which belong to main class of Tracheobionta and e.g. the subclass of meadow grasses (bamboo, reed, scouring rush, wild *angelica* and grass).

The composition may contain particulate or powdered material, such as sawdust, typically having particles with a size of less than 0.5 mm*0.5 mm*0.5 mm. Particulate or powdered material is characterised typically as material of a size in which the naked eye can no longer distinguish unique sides of the particle. Platy particles are easily recognizable as one dimension is recognizable by the naked eye as being larger than another. Granular particles, while having substantially equal dimensions, are of such dimension that their unique sides can be determined by the naked eye and oriented.

More particularly, particulate or powdered materials are of such a small or fine size that they cannot be easily oriented with respect to their neighbours. Granular and platy particles are of such as size that their sides are recognizable and orienttable.

The desired composition of the second component can be achieved by sifting woody particles through one or more meshes having one or more varying qualities. The desired composition can also be accomplished by other well known techniques in the art for sorting and separating particles in to desired categories. The desired composition may be the resultant composition of one sifting or separating process. The desired composition may also be a mixture of resultant compositions from several sifting or separation processes.

In one embodiment, the raw-material comprises wood particles, chips or granules, of any of the above mentioned wood species having a screened size of greater than 0.6 mm and up to 3.0 mm, in particular about 1 to 2.5 mm on an average.

According to one embodiment, the weight ratio of fibrous material (optionally including said powdered material) to the platy material (dry weight) is about 1:100 to 100:1, preferably about 5:100 to 50:50. In particular, the woody material derived from the platy wood particles forms at least 10%, preferably about 20 to 100%, in particular about 30 to 100%, of the total weight of the second component.

The woody material makes up at least and preferably more than 70% of the second component.

In addition to wood-based powdered materials, inorganic particulates or powdered materials such as mica, silica, silica gel, calcium carbonate and other calcium salts such as tricalcium orthophosphate, carbon, clays and kaolin may be present or added.

According to an alternative embodiment, a composite useful as an orthopedic material, comprises a first component formed by a polymer and a second component formed by a reinforcing material, wherein the first component comprises a thermoplastic polymer selected from the group of biodegradable polymers and mixtures thereof, and the second component comprises reinforcing fibres. Such fibers can be selected from the group for example of cellulose fibers, such as flax or seed fibers of cotton, wood skin, leaf or bark fibers of jute, hemp, soybean, banana or coconut, stalk fibers (straws) of hey, rice, barley and other crops including bamboo and grass. According to an interesting embodiment, the wood filler may consist of or consist essentially of fibres of the indicated kind. The polymer component can be any of the below listed polymers, caprolactone homo- or copolymers having a molecular weight of about 60000 g/mol up to 250,000 g/mol being particularly preferred.

The thermoplastic polymer and its properties will be discussed in more detail below, but for the sake of order it is pointed out that in all of the above mentioned embodiments, wherein various fillers are used as a second and a third and even fourth component of the composition, substantial advantages with respect to biodegradability and mechanical properties have been found using caprolactone polymers, in particular homopolymers, as thermoplastics. The particularly preferred polymer component is a caprolactone homopolymers having a molecular weight of above 80,000 g/mol. Specifically, caprolactone having a molecular weight of between 100,000 g/mol and 200,000 g/mol has been found to be advantageous both in terms of resultant properties and cost.

Before the woody particles are mixed with the thermoplastic polymer they can be surface-treated, e.g. sized, with agents who modify their properties of hydrophobicity/–hydrophobicity and surface tension. Such agents may introduce functional groups on the surface of the granules to provide for covalent bonding to the matrix. Even increased hydrogen bonding or bonding due to van der Waals forces is of interest. The woody particles can also be surface treated with polymer e.g. PCL having low viscosity and molar mass values to increase holding powers between wood and PCL having high viscosity value.

The wood material can be also coated or treated with anti-rot compound e.g. vegetable oil to improve its properties against aging and impurities.

The wood material can be dehydrated to make it lighter before mixing it with polymer. The mechanical and chemical properties of wood material can be improved with heat treatment, which is known to decrease e.g. swelling and shrinkage.

In the composition according to an aspect of the present invention, the first component of a first layer (the polymer) forms the matrix of the composite, whereas the microstructure of the second component in the composition in discontinuous. The particles of the second component can have random orientation or they can be arranged in a desired orientation. The desired orientation may be a predetermined orientation.

As mentioned above, according to a preferred embodiment, a polycaprolactone polymer (in the following also abbreviated "PCL") is used as a thermoplastic polymer in the first component of the composition. The polycaprolactone polymer is formed by repeating units derived from epsilon caprolactone monomers. The polymer may be a copolymer containing repeating units derived from other monomers, such as lactic acid, glycolic acid, but preferably the polymer contains at least 80% by volume of epsilon caprolactone monomers, in particular at least 90% by volume and in particular about 95 to 100% epsilon caprolactone monomers.

In a preferred embodiment, the thermoplastic polymer is selected from the group of epsilon-caprolactone homopolymers, blends of epsilon-caprolactone homopolymers and other biodegradable thermoplastic homopolymers, with 5-99 wt %, in particular 40 to 99 wt %, of an epsilon-caprolactone homopolymer and 1-95 wt %, in particular 1 to 60 wt %, of a biodegrable thermoplastic polymer, and copolymers or block-copolymers of epsilon-caprolactone homopolymer and any thermoplastic biodegradable polymer, with 5 to 99 wt %, in particular 40 to 99 wt % of repeating units derived from epsilon-caprolactone and 1 to 95 wt-%, in particular 1 to 60 wt-%, repeating units derived from other polymerizable material.

Examples of other biodegradable thermoplastic polymers include polylactides, poly(lactic acid), polyglycolides as well as copolymers of lactic acid and glycolic acid.

The first polymer component, in particular the epsilon caprolactone homo- or copolymer, has an average molecular weight of 60,000 to 500,000 g/mol, for example 65,000 to 300,000/mol, in particular at least 80,000 g/mol, preferably higher than 80,000 and up to 250,000.

The molding properties of the present invention can be determined by the average molecular weight ($M_n$) of the polymer, such as epsilon caprolactone homo- or copolymer. A particularly preferred molecular weight range for the $M_n$ value of PCL is from about 100,000 to about 200,000 g/mol.

The number average molar mass (Mn) and the weight average molar mass (Mw) as well as the polydispersity (PDI) were measured by gel permeation chromatography. Samples for GPC measurements were taken directly from the polymerization reactor and dissolved in tetrahydrofuran (THF). The GPC was equipped with a Waters column set styragel HR (1, 2 and 4) and a Waters 2410 Refractive Index Detector. THF was used as eluent with a flow rate of 0.80 ml/min at a column temperature of 35° C. A conventional polystyrene calibration was used. In determination of the water content of the monomer at different temperatures a Metroohm 756 KF Coulometer was used.

The properties of moldability of the present composition can also be determined by the viscosity value of the polymer. For an epsilon caprolactone homopolymer: when the inherent viscosity (IV)-value of PCL is less than 1 dl/g the composite is sticky, flows while formed and forms undesired wrinkles while cooling. When PCL having IV-value closer to 2 dl/g is used the composite maintains its geometry during molding on the patient and it may be handled without adhesive properties. Thus, IV values in excess of 1 dl/g are preferred, values in excess to 1.2 dl/g are preferred and values in excess of 1.3 dl/g are particularly suitable. Advantageously the values are in the range of about 1.5 to 2.5 dl/g, for example 1.6 to 2.1 dl/g. Inherent Viscosity values were determined by LAUDA PVS 2.55d rheometer at 25° C. The samples were prepared by solvating 1 mg of PCL in 1 ml chloroform ($CH_3Cl$).

A particularly important feature of the thermoplastic polymer is the viscosity which is relatively high, typically at least 1,800 Pas at 70° C., $1/10$ s; the present examples show that the viscosity can be on the order of 8,000 to 13,000 Pas at 70° C., 1/10 s (dynamic viscosity, measured from melt phase). Below the indicated value, a reinforced material readily wrinkles during forming it on a patient.

The thermoplastic material is preferably a biodegradable polymer (only) but also non-biodegradable polymers may be utilized. Examples of such polymers include polyolefins, e.g. polyethylene, polypropylene, and polyesters, e.g. poly(ethylene terephthalate) and poly(butylenes terephthalate) and polyamides. Combinations of the above biodegradable polymers and said non-biodegradable polymers can also be used. Generally, the weight ratio of biodegradable polymer to any non-biodegradable polymer is 100:1 to 1:100, preferably 50:50 to 100:1 and in particular 75:25 to 100:1. Preferably, the composite material has biodegradable properties greater, the material biodegrades quicker or more completely, than the thermoplastic material alone.

According to the invention, a polymer of the afore-said kind is preferably moldable at a temperature as low as +58° C., in particular at +65° C. or slightly above, and it can be mixed with wood particles or generally any porous material gaining increased rigidity of the formed composite. The polymer component, such as polycaprolactone homopolymer, defines the form of the splinting material against the skin.

In one embodiment, the modulus (Specific Young's modulus), at ambient temperature, of the polymer component is greater than 300 MPa. By compounding the polymer with the wood component, the modulus can be improved, for example it can be about 350 to 2000 MPa for the composition. These parameters have been measured for sheets of the polymer material (i.e. without the textile layer), having a thickness of 4 mm obtained by pressing together 4 polymer sheets having a thickness of 1 mm at a temperature of about 100° C. For individual polymer layers of a thickness of about 1 mm, the modulus (Specific Young's modulus) at ambient temperature (about 25° C.) will typically be greater about 150 MPa, in particular greater than about 200 MPa. By compounding such thinner layers with the wood component disclosed herein the modulus will become about 250 to 2000 MPa.

The present material contains a significant portion of wood granules having a particle size greater than the micrometer range, for example a size of about 0.1 mm to 10 mm. When the material is shaped into a ~1 mm sheet, (at least most of) the wood granules become oriented in two dimensions within forming of the thermoplastic material into sheets.

According to a preferred embodiment, the present method of producing a composite useful as one layer of a bandage material comprises the steps of mixing together 10 to 100 parts, preferably 50 to 100 parts, by weight of a first component formed by a polymer selected from the group of biodegradable polymers and mixtures thereof, and 1 to 100 parts, preferably 10 to 50 parts, by weight of a second component formed by a reinforcing material, present in the form of platy wood particles.

The molten polymer mass containing a mixture of biopolymer and reinforcing platy or granular particles can be shaped manually or, according to a preferred embodiment by moulding in a mould.

In one embodiment, composites having the following mechanical properties were used in the composite layer (it should be pointed out that the properties have been determined for a composite layer having a thickness of 4 mm): Composites containing wood less than 30 weight-% revealed adhesive forces close to 400 N and the composites containing wood over 40 weight-% revealed adhesive forces below 10 N when pressure of ~0.1 bar was used (correspond to a gentle press with palm). The former having adhesion forces above 100 N can be considered to be "everlasting" bond which can't be broken without casting saw. The latter composites having adhesion forces less than 10 N can be easily separated apart by hands.

The latter value is generally applicable to materials of the present kind irrespective of the thickness of the composite material.

These adhesive forces will further on decrease when a layer of a textile is placed between the composite layers, which is the situation when the bandage of the present invention is coiled circumferentially around limb.

The manufacturing process of the bandage material can, on an industrial scale, may be carried out as follows:

In a first step wood chips or granules and plastic granules are mixed to form a uniform blend before pouring into the feed hopper of an extruder. The mixing process can be carried out also by feeding of the virgin materials to the extruder directly by using separate feeding hoppers.

The compounding is then carried out in, e.g., an extruder, in particular a single or dual screw extruder. In the compounding process the screw extruder profile of the screw is preferably such that its dimensions will allow relatively large wood chips to move along the screw without crushing them. Thus, the channel width and flight depth are selected so that the formation of excessive local pressure increases, potentially causing crushing of the wood particles, are avoided. The temperature of the cylinder and the screw rotation speed are also selected such as to avoid decomposition of wood chip structure by excessively high pressure during extrusion. For example a suitable barrel temperature can be in the range of about 110 to 150° C. from hopper to die, while the screw rotation speed was between 25-50 rpm. These are, naturally, only indicative data and the exact settings will depend on the actual apparatus used.

The density of composite manufactured for example lies in the range of about 600 to 1050 kg/m$^3$, for example 600 to 850 kg/m$^3$, depending on the weight percent of wood in material.

The manufacturing process of the composite material is described in more detail in our co-pending patent application PCT/FI2008/050187, titled "Method of Producing a Composite Material", the content of which is herewith incorporated by reference.

To allow for processing in the next step (the forming of the bandage), it is preferred to make the composite layer, having typically a thickness of 0.5 to 1.5 mm, self-supporting so that it capable of forming a band which can be fed as such from the extruder to a calandering device.

The thin layer of the composite material is combined, preferably immediately after melt processing, with a textile layer to form the bandaging material. In the method of manufacture, the melt composite material is therefore provided in the form of a first layer having a linear structure having a width (W), a length (L) and a thickness (T), the ratio of length to width, L/W, being at least 3:1, for example at least 5:1, in particular at least 6:1 or at least 8:1, for example 10:1 up to about 100:1; a second layer of a textile material having a first and a second surface is provided as a separate web; the first and the second layers are fitted in superposed relationship; and then pressed against each other at a temperature in excess of 80° C. so as to provide a bandaging material.

The two layers can be pressed together by separately feeding them to a calander, the textile from a textile roll and the composite band from a melt extruder or a similar processing machine.

According to one embodiment, the textile layer is an elastic material, for example a fabric or gauze or felt which is capable of being elastically elongated in one or several directions.

Pressing of a first layer and a second layer to each other is preferably carried without pre-stretching of layers for maintaining elasticity of the bandage material at application temperature.

By selecting the molecular weight/IV of the thermoplastic component of the composite as discussed above, the polymer melt will primarily not migrate into the textile fibres or thread to impregnate the material. Therefore, in the bandaging material, the first layer comprising the composite material will be essentially attached only to the first surface of said second layer (the textile). The textile will therefore not be fully embedded in the composite material but rather form a surface layer of the bandage. It is preferred that composite layers are not in direct contact with each other at application temperature, hence allowing easy foiling and un-foiling procedures of the bandage.

In an embodiment, the bandaging material is capable of being coiled to a roll having a diameter of maximally 80 mm, and the innermost coil of less than 20 mm, preferably less than 15 mm.

The textile material of the second layer comprises a network of natural or artificial fibers or combinations thereof, formed by weaving, knitting, crocheting, knotting, wet felting or a fabric made through weaving, knitting, spreading, crocheting or bonding. Preferably the textile material is elastically extensible, i.e. it exhibits elasticity in at least one dimension, in particular in two dimensions at least—it is advantageous that the textile material is flexible in the direction of its width and length.

The textile material can comprise fibres of cellulose materials (e.g. cotton), viscose, linen, flax, hemp, jute and other natural fiber materials. It can also comprise fibres of synthetic fibres such as polyesters, polyamides, polyurethanes, polynitrile, ABS, polyolefins (such as polypropylene) as well as copolymeric materials, such as elastomeric materials and thermoelastic polymers (TPEs). Of the latter materials, TPEs having melting or softening points above the melting point of the PCL are particularly interesting.

According to a preferred embodiment, the extensibility of a textile layer, in particular when it is present in the form of a fabric or a gauze, may amount to 1% or more, e.g. 5 to 90%, in particular 50% or less, preferably about 5 to 45% in the warp direction. This means that the unextended fabric may be extended in the warp direction from 100 to e.g. 105-150%. In the weft direction, extensibility may also amount to 1% or more, e.g. 5 to 90%, in particular 50% or less, preferably about 5 to 45%. This means that the fabric can be stretched from 100 to 105 or as much as 190%.

Notwithstanding the above, the textile layers generally having elastic elongation of up to 200% and even more can be used in the invention, although modest elasticity of about 10 to 40% has been found satisfactory and advantageous in practice. Examples of highly elastic textile products include textiles with a high content of latex or elastane such as so-called Coban band(ages) and ace bandages.

When polyamide or polyester or polypropylene fibers are used for the manufacture of the warp- and weft threads, the size of the warp thread size can be generally in the range from about 30 to 80 tex, for example about 40 to 60 tex, and size of the weft thread can be about 10 to 50, for example about 20 to 40 tex.

As mentioned above, the structure of the textile layer is preferably loose, such that it is reminiscent of a gauze or net which is freely breathable. A porous and permeable textile layer having a surface weight of about 0.5 to 250 g/m$^2$ is preferred. In particular, the textile layer is light-weight having a surface weight in the range of 1 to 100 g/m$^2$, in particular about 1.5 to 50 g/m$^2$.

At a temperature above the solidification point but below 80° C., the bandaging material typically exhibits only modest interlayer adhesion when coiled to a roll without force during manufacturing process. Still the interlayer adhesion is sufficient for allowing overlapping layers to be adhered to each other when the bandage is used as a cast or splint for immobilization purposes.

The bandaging material can be uncoiled smoothly by hand without changes in dimensions followed by subsequent applying of it around limb at application temperature. When appropriate force is used during applying of bandage, the inter- and intralayer self-adhesion of the bandage will be excellent and no de-lamination will occur at ambient temperature (typically 10 to 40° C.) within the healing period of the injured limb.

In one embodiment, the composite material is punctuated or perforated for diminishing self-adhesion feature during coiling and un-coiling procedures and for improving breathability. Thus, in this embodiment, the bandaging material is provided with a plurality of openings or apertures which extend through the material to provide a perforated structure.

The composite surface may also be contoured three-dimensionally for improving mechanical strength and for diminishing self-adhesion feature during coiling and un-coiling procedures. Thus in one particularly advantageous embodiment, the bandaging material is embossed. Embossing is typically carried out mechanically to provide embossing depressions, having a maximum depth in the range of 0.01 to 5 mm, typically about 0.1 to 3 mm, in particular about 0.5 to 2 mm. The diameter of the depressions is typically about 0.1 to 10 mm, in particular about 0.5 to 5 mm. There are typically about 0.5 to 100 depressions per square cm of the material, in particular about 1 to 20 depressions per cm$^2$.

Embossing can be carried out by using embossing rolls that work by pressing onto the bandaging material a depressed pattern in a nip.

The pattern of the embossing depressions can vary freely. Thus, the web surface can be embossed with traditional, at least essentially circular or rhomibic or squerical depressions, but it is also possible to provide a three-dimensional pattern such as a honeycomb pattern.

After pressing procedure of the layers the bandage tape may be coiled to a roll form at a temperature above the solidification point but below 150° C.

Based on the above, the composite material of the first layer exhibits typically, after pressing together with the textile material of the second layer, at a temperature higher than 80° C., so strong adhesion to the textile material of the second layer, that the banding material can be coiled and uncoiled without de-attachment of the first layer of the second layer.

In a preferred embodiment, the composite material of the first layer, exhibits after pressing together with the textile material at a temperature in excess of about 90° C., so strong tackiness towards the textile material of the second layer, that banding material can be coiled, and at a temperature above solidification but below 80° C. so modest interlayer adherence that it can be uncoiled without de-attachment of the first layer of the second layer.

Further, the bandaging material typically exhibits at a temperature above the solidification point but below 80° C., modest to small self-adhesion, so that the bandaging material can be uncoiled by hand without changes in dimensions of the bandaging material.

At a manipulation temperature of 58 to 80° C. or less than 80° C., typically about +65° C. or slightly more, the present bandaging material can be manipulated and manually shaped for up to 10 minutes and it is typically pliable for 1-10 minutes after the finishing of heating. The material hardens entirely in one hour.

The dimensions for the rolled bandage cast can be: length 0.5-10 m, thickness 0.5-1.5 mm and width 2.5-15 cm.

To achieve rapid solidification of the material, a cooling spray or a cooling gel or wrap can be used.

Generally, the present bandage can be used to form an exo-skeletal device on a portion of an animals or human beings body or body part. In the method a bandage can be used which, generally, comprises a textile layer and, attached to the textile layer, a thermoplastic polymer layer containing platy or granular wood particles, said bandage exhibiting strong intralayer adhesion between the textile layer and the thermoplastic polymer layer, and a modest interlayer adhesion.

The exo-skeletal device can be used as a shin-pad, wrist guard or even a foot bed for footwear. However, it is especially well suited as a splint or cast structure to immobilize, or partially immobilize a portion of an animals or humans body or body part.

The bandage is heated before use. The heater may have an adjustable thermostat or may be preprogrammed to heat automatically to the desired temperature. Ideally, the heater will have a heating element capable of heating an entire bandage uncoiled or in the form of a roll evenly and completely. The size of the heater should be sufficient enough to handle the size of the bandaging material. To speed up the heating procedure of the roll air circulation may be used.

In cases where the heating element is other than one specifically tailored to the present composite material it can be selected from the range of known heating elements including contact heaters, convection heaters, chemical heating and the like, including microwave ovens.

Once the bandage has been heated to the desired temperature, as discussed above, then the material can be coiled circumferentially on the patient in the desired location to form the exo-skeletal device. The advantage of the present material is that it can be handled by hand without any protective requirement such as gloves. Equally important is that the material can be formed directly against the patient's skin. However, it can be advantageous to have some material, such as gauze or other cloth/cloth like material, directly in contact with the patients skin.

With the bandaging material still pliable and moldable, it can be fit to contour the patient's body part nearly or exactly. If the material has lost its desired moldability, then it can be uncoiled, reheated and likewise moved to the new location. One of the particular advantages of the present material is that it can be heated and cooled many times without degrading its mechanical properties.

When the bandage is located properly and molded to the desired form, then it can be allowed to cool to a temperature where it can be removed but maintain its shape. The cooling may be accomplished by allowing the ambient conditions to reduce the temperature of the material or the cooling may be aided by spraying the material with water or another chemical to speed up the cooling.

In the case of a splint, bandage may be wrapped around it and the adhesive properties of the not yet cooled composite material will hold the splint in place, therefore facilitating additional immobilization of the intended body part. The best immobilization/adhesion is achieved when a first layer of the bandage is placed against the splint.

When the bandage is no longer needed for its previous purpose it can be uncoiled, reheated and removed if necessary, and either coiled or stored as is until the next time when it is required. The resultant material has the same mechanical properties in subsequent uses as in previous uses and is therefore not degraded through multiple uses.

The following non-limiting examples illustrate embodiments of manufacturing a composite/textile bandaging tape Example 1

Manufacturing

A commercially available polycaprolactone under tradename CAPA 6800 (Perstorp Ltd, Sweden) was mixed with a batch of saw dust received from a local saw mill (average particle size 2 mm). The measured melt flow index for the polymers was 3 g/10 (named PCL-3). This homopolymer exhibits significantly lowere melt flow rate than measured for another polycaprolactone homopolymer, about 7 g/10 min (named PCL-7). The melt flow indeces were measured at 150° C. and with a weight of 2.16 kg.

Mixing was carried out by shaking few minutes with various levels wood (20, 40 and 60 weight percent) and PCL-3 (80, 60 and 40 weight percent) in a plastic box followed by pouring the blend to the extruder.

The extrudate was collected and cut to 80-120 cm round profiles, diameter approximately 5 mm. The temperatures of different heating zones were kept constant at 130° C. The temperature of the die was slightly lower being 110° C. The composite bars were pressed with a calander to ~1.5 mm thick composite tapes. In the same process the width of the bar increased to 3.5 cm. By combining two melted composite bars together, followed by calandering, wider (~5 cm) composite tapes were achieved. The temperatures of the calander cylinders were kept close to 100° C. to verify good adhesion between the bandage and composite.

The end-products were achieved by coating the composite tapes with bandage by using calandering techniques. The calandering process was repeated as many times as required to achieve ~1.3 mm thick and smooth surface end-product. The resulted composite tapes are listed in Table 1.

TABLE 1

Manufactured WPC casting tapes

| Code | bandage | wood | wood (%) |
|---|---|---|---|
| SP13AP20 | cotton gauze | spruce | 20 |
| SP13SCB20 | softcrepe bandage | spruce | 20 |
| SP13MH20 | mollelast haft | spruce | 20 |
| SP13C20 | coban | spruce | 20 |
| SP13MH40 | mollelast haft | spruce | 40 |
| SP13T40 | tubinette | spruce | 40 |
| SP13ET40 | elastic tricot | spruce | 40 |
| SP13SCB40 | softcrepe | spruce | 40 |
| SP13AP40 | cotton gauze | spruce | 40 |
| SP1340 | — | spruce | 40 |
| SP13C60 | coban | spruce | 60 |
| SP13SCB60 | softcrepe | spruce | 60 |
| SP13EA60 | elastic tricot | spruce | 60 |
| SP13MH60 | mollelast haft | spruce | 60 |

TABLE 1-continued

Manufactured WPC casting tapes

| Code | bandage | wood | wood (%) |
|---|---|---|---|
| SP13GB60 | gauge bandage | spruce | 60 |
| MR35MH60 | mollelast haft | aspen | 60 |
| MR3560 | — | aspen | 60 |
| MR35SCB60 | softcrepe | aspen | 60 |

Example 2

Applicability Experiments

The manufactured composite-textile bandages were tested for the coiling, uncoiling and adhesion properties. All the casting tapes consisting of composite having 20 weight percent wood were unsatisfactory for use due to too high self-adhesive forces. The materials were in practice impossible to uncoil when heated to application temperature.

The materials comprising a composite with 40 w-% wood and 60 w-% PCL-3 exhibited improved properties. Slightly elastic (elastic elongation of ~15%) textile (Mollelast haft) with these composites provided a most satisfactory bandage material for casting purposes. At application temperature of 65° C. the self-adhesive force was reasonable for smooth coiling and un-coiling and elasticity of the tape was on such a level that neither tearing of the material nor wrinkle formation was observed. In addition, it revealed excellent self-adhesion and adhesion to OMNICAST-splint comprising a blank of about 3 mm thickness comprised primarily of the composite material after hardening. As such the material was light enough and no punctuation is required.

Based on the user studies by orthopedic professionals, casting tapes consisting of composite having 60 weight percent wood gave rise to some tearing of the composite during un-rolling and setting at application temperature.

According to evaluation the composites coated with highly elastic (over 100%) bandage (cotton gauze) were unsatisfactory for practical purposes because they did not sufficiently maintain their dimensions during setting at application temperature. On the other hand, composites coated with rigid non-elastic bandages (gauge bandage) gave cause to the formation of some wrinkles during hardening process.

Of the materials in Table 1, the specimen identified with the label SP13MH40 is particularly interesting because it exhibited the following optimal application properties:
  easy to unroll
  does not tear during setting
  pliable at application temperature
  good self-adhesion after hardening
  can be cut with standard scissors
  can be handled without gloves
  can be molded after setting
  is slightly elastic (~15%)
  non-toxic
  does not form wrinkles during setting.

The invention claimed is:

1. An orthopaedic bandaging material in the form of a linear structure having a width (W), a length (L) and a thickness (T), the ratio of length to width, L/W, being at least 3:1, said material comprising
  a first layer of a composite material with a first component formed by a polymer and a second component formed by a reinforcing material distributed throughout the first polymer, wherein
    the first component comprises a thermoplastic polymer including a first polymer component having an inherent viscosity (IV) of 1.5 dl/g to 2.5 dl/g al 25° C. for 1 mg of PCL solvatated in 1 ml chloroform ($CH_3Cl$), and
    the second component comprises a woody material derived from platy or granular wood particles having a minimum average size in one dimension of 0.1 mm wherein the individual wood panicles have at least two dimensions greater than 0.6 mm and one greater than 0.1, said wood particles having an average volume of at least 0.03 $mm^3$,
    wherein the content of the composite material is 25 to 50 parts by weight of the woody material, the weight of the woody material being calculated based on the dry weight of said wood material, and
  a second layer of a textile material having a first and a second surface; said first layer being superposed on said second layer in such a way that said first layer is essentially attached only to the first surface of said second layer,
  wherein the bandaging material is provided in the form of a roll having at least 2 coils and being capable of being coiled and uncoiled at an application temperature without de-attachment of the first layer from the second layer.

2. The bandaging material according to claim 1, wherein the composite material of the first layer exhibits, after pressing together with the textile material of the second layer, at a temperature higher than 80° C., so strong adhesion to the textile material of the second layer, that the bandaging material can be coiled and uncoiled without de-attachment of the first layer from the second layer.

3. The bandaging material according to claim 1, wherein the material properties of the first and second layers are such that, at a temperature above a solidification point but below 80° C., the bandaging material is capable of modest to small self-adhesion, so that the bandaging material can be uncoiled by hand without changes in dimensions of the bandaging material.

4. The bandaging material according to claim 1, wherein said bandaging material is capable of being uncoiled only because of the self-adhering first layer and non-adhering second layer.

5. The bandaging material according to claim 1, capable of being coiled to a roll having a diameter of maximally 80 mm, and an innermost coil of less than 20 mm.

6. The bandaging material according to claim 1, wherein the textile material consists of a network of natural or artificial fibers formed by weaving, knitting, crocheting, knotting, wet felting or fabric made through weaving, knitting, spreading, crocheting or bonding.

7. The bandaging material according to claim 6, exhibiting elasticity in at least one dimension.

8. The bandaging material according to claim 6, comprising a loose textile with an open and/or porous structure.

9. The bandaging material according to claim 1, wherein the woody material derived from the platy wood particles forms at least 10% of the total weight of the second component.

10. The bandaging material according to claim 1, wherein the first component forms a matrix of the composite, and the microstructure of the second components is discontinuous.

11. The bandaging material according to claim 1, comprising 40 to 80 parts by weight of a thermoplastic polymer component.

12. The bandaging material according to claim 1, wherein the thermoplastic polymer is selected from the group consisting of epsilon-caprolactone homopolymers, blends of epsilon-caprolactone homopolymers and other biodegradable thermoplastic homopolymers, with 5-99 wt % of an epsilon-caprolactone homopolymer and 1-95 wt % of a biodegrable thermoplastic polymer, and copolymers of epsilon-caprolactone homopolymer and any thermoplastic biodegradable polymer, with 5 to 99 wt % of repeating units derived from epsilon-caprolactone and 1 to 95 wt % repeating units derived from other polymerizable material.

13. The bandaging material according to claim 1, wherein a density of the composition is at least 5% less than that of the epsilon-caprolactone homopolymer.

14. The bandaging material according to claim 1, wherein the individual wood particles have at least two dimensions greater than 0.6 mm and one greater than 0.1, said wood particles having an average volume of at least 0.03 mm$^3$.

15. The bandaging material according to claim 1, wherein the bandaging material is provided with a plurality of openings or apertures which extend through the material to provide a perforated bandage.

16. The bandaging material according to claim 1, having a width of 10 to 150 mm, a length of 400 to 10,000 mm and a thickness of 0.1 to 1.5 mm.

17. An orthopaedic bandaging material in the form of a linear structure having a width (W), a length (L) and a thickness (T), the ratio of length to width, L/W, being at least 3:1, said material comprising a first layer of a composite material with a first component formed by a polymer and a second component formed by a reinforcing material distributed throughout the first polymer, wherein
 the first component comprises a thermoplastic polymer, including a first polymer component having an inherent viscosity (IV) of 1.5 dl/g to 2.5 dl/g at 25° C. for 1 mg of PCL solvated in 1 ml chloroform (CH3Cl), and
 the second component comprises a woody material derived from platy or granular wood particles having a minimum average size in one dimension of 0.1 mm; wherein the individual wood particles have at least two dimensions greater than 0.6 mm and one greater than 0.1, said wood particles having an average volume of at least 0.03 mm3,
 wherein the content of the composite material is 25 to 50 parts by weight of the woody material, the weight of the woody material being calculated based on the dry weight of said wood material, and
a second layer of a textile material having a first and a second surface; said first layer being superposed on said second layer in such a way that said first layer is essentially attached only to the first surface of said second layer, and
wherein the composite material of the first layer exhibits, after pressing together with the textile material of the second layer, at a temperature higher than 80° C., so strong adhesion to the textile material of the second layer, that the banding material can be coiled and uncoiled without de-attachment of the first layer of the second layer.

* * * * *